United States Patent
Keller

(10) Patent No.: US 8,852,186 B2
(45) Date of Patent: Oct. 7, 2014

(54) MICROWAVE SENSING FOR TISSUE SEALING

(75) Inventor: Craig A. Keller, Boulder, CO (US)

(73) Assignee: Covidien LP, Mansfield, MA (US)

( * ) Notice: Subject to any disclaimer, the term of this patent is extended or adjusted under 35 U.S.C. 154(b) by 535 days.

(21) Appl. No.: 13/205,860

(22) Filed: Aug. 9, 2011

(65) Prior Publication Data

US 2013/0041361 A1 Feb. 14, 2013

(51) Int. Cl.

| | | |
|---|---|---|
| A61B 18/14 | (2006.01) | |
| A61B 18/18 | (2006.01) | |
| A61B 5/05 | (2006.01) | |
| A61B 5/00 | (2006.01) | |
| A61B 18/12 | (2006.01) | |
| A61B 18/00 | (2006.01) | |

(52) U.S. Cl.
CPC ..... *A61B 18/1815* (2013.01); *A61B 2018/1861* (2013.01); *A61B 18/1445* (2013.01); *A61B 2018/00642* (2013.01); *A61B 5/0507* (2013.01); *A61B 5/4836* (2013.01); *A61B 2018/0063* (2013.01); *A61B 2018/00702* (2013.01); *A61B 2018/00785* (2013.01); *A61B 18/1206* (2013.01)
USPC .......................................................... 606/52

(58) Field of Classification Search
USPC ............................ 606/32–34, 38–41, 49–52; 607/101–102, 154, 156
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| 4,315,510 A | 2/1982 | Kihn |
| 4,597,379 A * | 7/1986 | Kihn et al. ..................... 606/40 |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

European Search Report for European Application No. 12179628.8 dated Sep. 20, 2012.

(Continued)

*Primary Examiner* — Michael Peffley

(57) ABSTRACT

A system for monitoring the target tissue during a tissue sealing procedure is disclosed. The system includes a forceps having opposing jaw members movable from a first position in spaced relation relative to one another to at least one subsequent position wherein the jaw members cooperate to grasp the tissue therebetween. Each of the jaw members includes a sealing member. The system also includes a generator coupled to the sealing members so that therapeutic energy is delivered to the target tissue. The generator includes an output stage configured to generate therapeutic energy and a microwave detector configured to measure reflected and/or absorbed microwave signals. The monitored microwave signals may be either the therapeutic energy signal or a separate non-therapeutic microwave monitoring signal. The generator also includes a controller operatively coupled to the microwave detector. The controller is configured to determine the state of the tissue based on the reflected and/or absorbed microwave signals and to control the delivery of therapeutic energy from the generator to tissue based on the microwave measurements.

13 Claims, 4 Drawing Sheets

(56) References Cited

U.S. PATENT DOCUMENTS

| | | | |
|---|---|---|---|
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| 6,033,401 A | 3/2000 | Edwards et al. | |
| D424,694 S | 5/2000 | Tetzlaff et al. | |
| D425,201 S | 5/2000 | Tetzlaff et al. | |
| H1904 H | 10/2000 | Yates et al. | |
| 6,224,593 B1* | 5/2001 | Ryan et al. | 606/41 |
| 6,230,060 B1* | 5/2001 | Mawhinney | 607/101 |
| 6,233,490 B1* | 5/2001 | Kasevich | 607/101 |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| 6,679,882 B1 | 1/2004 | Kornerup | |
| D493,888 S | 8/2004 | Reschke | |
| 6,773,409 B2 | 8/2004 | Truckai et al. | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| 7,192,427 B2* | 3/2007 | Chapelon et al. | 606/33 |
| D541,418 S | 4/2007 | Schechter et al. | |
| D541,611 S | 5/2007 | Aglassinge | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 2004/0210282 A1 | 10/2004 | Flock et al. | |
| 2010/0036379 A1 | 2/2010 | Prakash et al. | |
| 2010/0094271 A1 | 4/2010 | Ward et al. | |
| 2010/0249769 A1 | 9/2010 | Nau, Jr. et al. | |
| 2011/0125148 A1* | 5/2011 | Turner et al. | 606/33 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| EP | 1 186 274 B1 | 4/2006 |
| EP | 2364660 A1 | 9/2011 |
| EP | 2457532 A1 | 5/2012 |
| JP | 61-501068 | 9/1984 |
| JP | 6-502328 | 3/1992 |
| JP | 5-5106 | 1/1993 |
| JP | 5-40112 | 2/1993 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2004-517668 | 6/2004 |
| JP | 2004-528869 | 9/2004 |
| SU | 401367 | 11/1974 |
| WO | WO 00/36986 | 6/2000 |
| WO | WO 01/15614 | 3/2001 |
| WO | WO 01/54604 | 8/2001 |
| WO | WO 2005/110264 | 11/2005 |
| WO | WO2012076844 A1 | 6/2012 |

OTHER PUBLICATIONS

U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Horner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.

(56) References Cited

OTHER PUBLICATIONS

U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Towney.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.

(56) References Cited

OTHER PUBLICATIONS

Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Intl Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.

(56) References Cited

OTHER PUBLICATIONS

Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

MICROWAVE SENSING FOR TISSUE SEALING

BACKGROUND

1. Technical Field

The present disclosure relates to forceps for sealing various types of tissue. More particularly, the present disclosure relates to open, laparoscopic or endoscopic forceps for tissue sealing that utilize microwave energy to determine completeness of the tissue seal.

2. Description of the Related Art

In many surgical procedures, body vessels, e.g., blood vessels, ducts, adhesions, fallopian tubes, etc. are sealed to defunctionalize or close the vessel. Traditionally, staples, clips or sutures have been used to close a body vessel. However, these traditional procedures often leave foreign body material inside a patient. In an effort to reduce foreign body material left within the patient and to more effectively seal the body vessel, energy techniques that seal by heat processes have been employed.

A forceps is particularly useful for sealing tissue and vessels since forceps utilizes mechanical action to constrict, grasp, dissect and/or clamp tissue. Current vessel sealing procedures utilize a unique combination of pressure, gap control and energy to close and seal tissue and body vessels. The combination of heating and applied pressure provides a uniform, controllable seal with minimum collateral damage to body tissue.

SUMMARY

According to one embodiment of the present disclosure, a system for monitoring tissue state during a tissue sealing procedure is disclosed. The system includes a forceps including opposing jaw members movable from a first position in spaced relation relative to one another to at least one subsequent position wherein the jaw members cooperate to grasp tissue therebetween; and a generator coupled to at least one of the jaw members, the generator including: an output stage configured to generate therapeutic energy and non-therapeutic microwave monitoring signals; a microwave detector configured to measure at least one of absorbed or reflected non-therapeutic microwave monitoring signals; and a controller operatively coupled to the microwave detector, the controller configured to determine state of the tissue based on at least one of the absorbed or reflected non-therapeutic microwave monitoring signals and to control the delivery of therapeutic energy from the generator to tissue based the state of the tissue.

According to another embodiment of the present disclosure, a system for monitoring tissue state during a tissue sealing procedure is disclosed. The system includes a forceps including opposing jaw members configured to grasp tissue therebetween, at least one of the jaw members including at least one microwave probe; and a generator coupled to the at least one microwave probe, the generator including: a microwave output stage configured to generate therapeutic microwave energy; a microwave detector configured to measure at least one of absorbed or reflected therapeutic microwave energy; and a controller operatively coupled to the microwave detector, the controller configured to determine state of the tissue based on at least one of the absorbed or the reflected therapeutic microwave energy and to control the delivery of the therapeutic energy from the generator to tissue based the state of the tissue.

A method for monitoring tissue during a tissue sealing procedure is also contemplated by the present disclosure. The method includes the steps of supplying therapeutic energy and non-therapeutic microwave monitoring signals to a forceps, the forceps including opposing jaw members configured to grasp tissue therebetween; measuring reflected non-therapeutic microwave monitoring signals; and controlling the delivery of therapeutic energy based on reflected non-therapeutic microwave monitoring signals.

Another method for monitoring tissue state during a tissue sealing procedure is also contemplated by the present disclosure. The method includes the steps of supplying therapeutic microwave energy to a forceps. The forceps include opposing jaw members configured to grasp tissue therebetween. The method also includes the steps of measuring the reflected and/or absorbed therapeutic microwave signals and controlling the delivery of the therapeutic microwave energy based on reflected and/or absorbed microwave monitoring energy.

BRIEF DESCRIPTION OF THE DRAWINGS

Various embodiments of the present disclosure are described herein with reference to the drawings wherein.

DETAILED DESCRIPTION

Figure 1:
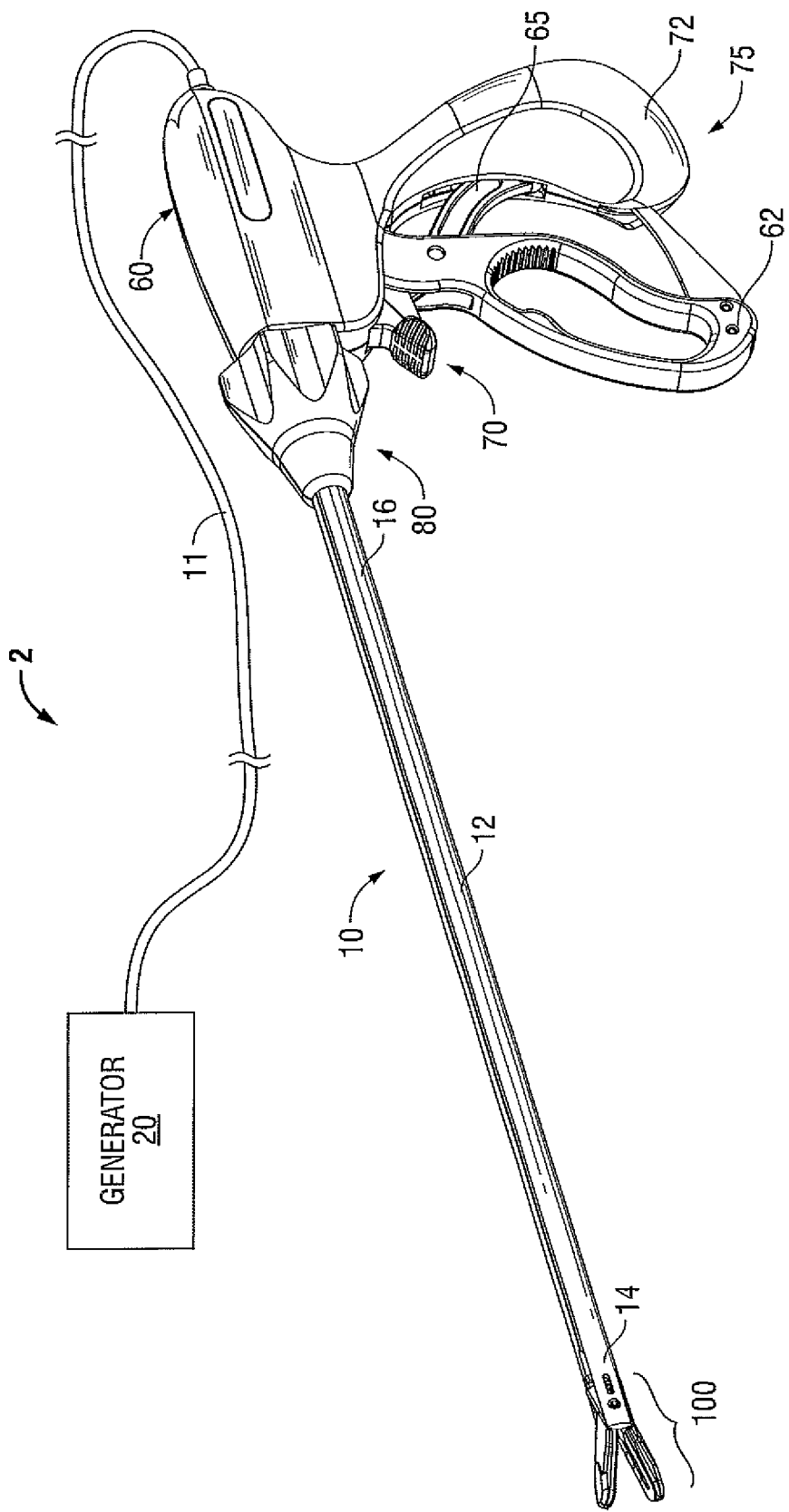
FIG. 1 is a perspective view of a tissue sealing system including a forceps and an energy generator according to one embodiment of the present disclosure.

Various embodiments of the present disclosure are described hereinbelow with reference to the accompanying drawings. Well-known functions or constructions are not described in detail to avoid obscuring the present disclosure in unnecessary detail. Those skilled in the art will understand that the present disclosure may be adapted for use with either an endoscopic instrument or an open instrument; however, different electrical and mechanical connections and considerations apply to each particular type of instrument. The novel aspects, with respect to vessel and tissue sealing are generally consistent with respect to both the open and endoscopic designs. In the drawings and in the description that follows, the term "proximal", as is traditional, will refer to the end of the forceps that is closer to the user, while the term "distal" will refer to the end of the forceps that is further from the user.

Referring now to FIG. 1, a tissue sealing system 2 according to the present disclosure is shown including a forceps 10 coupled to a generator 20. The forceps 10 is adapted to seal tissue using high frequency RF energy or microwave energy. The generator 20 may also be configured to output various types of energy, such as high frequency RF energy (e.g., from about 100 kHz to about 300 MHz) and microwave energy (e.g., from about 300 MHz to about 10,000 MHz).

In one embodiment, the generator 20 includes a microwave detector (e.g., microwave detector 22). The microwave detector 22 is coupled to the forceps 10 and is configured to determine progression of the sealing process based on measurements of microwave energy reflected and absorbed by the tissue. Microwave energy of either non-therapeutic or therapeutic type is supplied to the tissue grasped by the forceps 10.

As used herein the term "therapeutic" denotes RF or microwave energy applied to the tissue for treating tissue. In particular, therapeutic energy denotes sufficient energy for increasing the temperature of the tissue and to cause thermodynamically irreversible processes to occur therein. As used herein, the term "non-therapeutic" denotes microwave measurement signals that are intended only to measure tissue properties and generally provide little to no therapeutic effect on the tissue. Since the total energy delivered to the tissue by a therapeutic or non-therapeutic signal depends on the rate of energy deposition into the tissue as well as on the duration of the signal, the distinction between therapeutic and non-therapeutic signals is due to the power of the signal, the duration of the signal, and the efficiency with which the signal is coupled to the tissue (e.g., a high power signal may cause very little heating if only a small fraction of the power in the signal is absorbed by the tissue). In embodiments, non-therapeutic signals may provide from about 0.1% to about 10% of the total energy supplied to the tissue by therapeutic signals.

Generally, the present disclosure provides a system and method for microwave monitoring of tissue during a tissue sealing procedure, by measuring or monitoring the interaction of a microwave signal with the target tissue. Measurements might include reflection from and/or absorption of microwave energy by the tissue. Processing of the measurements allows a more accurate analysis of how the tissue is transformed during the fusion/sealing process. Such an analysis provides for improved tracking of the tissue modifications that lead to high quality seals. The processed data obtained during the fusion process may be incorporated into a suitable feedback loop controlling the delivery of energy (e.g., RF or microwave) to the tissue so that the optimum tissue transformations are obtained.

In one embodiment, the interaction of a therapeutic microwave signal with the target tissue can be monitored. In another embodiment, non-therapeutic microwave monitoring signals may be applied either simultaneously with the therapeutic energy or be interleaved therewith. The measured signal interaction (or the changes therein) may then be used as a control parameter in a tissue sealing algorithm to control energy delivery.

Without being constrained by any particular theory, it is believed that dehydration of the target tissue is an important part of transforming the target tissue into a strong seal. Electromagnetic radiation at microwave frequencies interacts with tissue primarily through the water contained in the tissue. This makes microwave techniques very sensitive to the amount of water contained in the tissue (e.g., the hydration of the tissue). Since microwave energy can also be used to heat tissue containing water, microwave based monitoring of the target tissue can potentially utilize the same transmission structures used to transport the therapeutic microwave signal to the target tissue.

Figure 2:
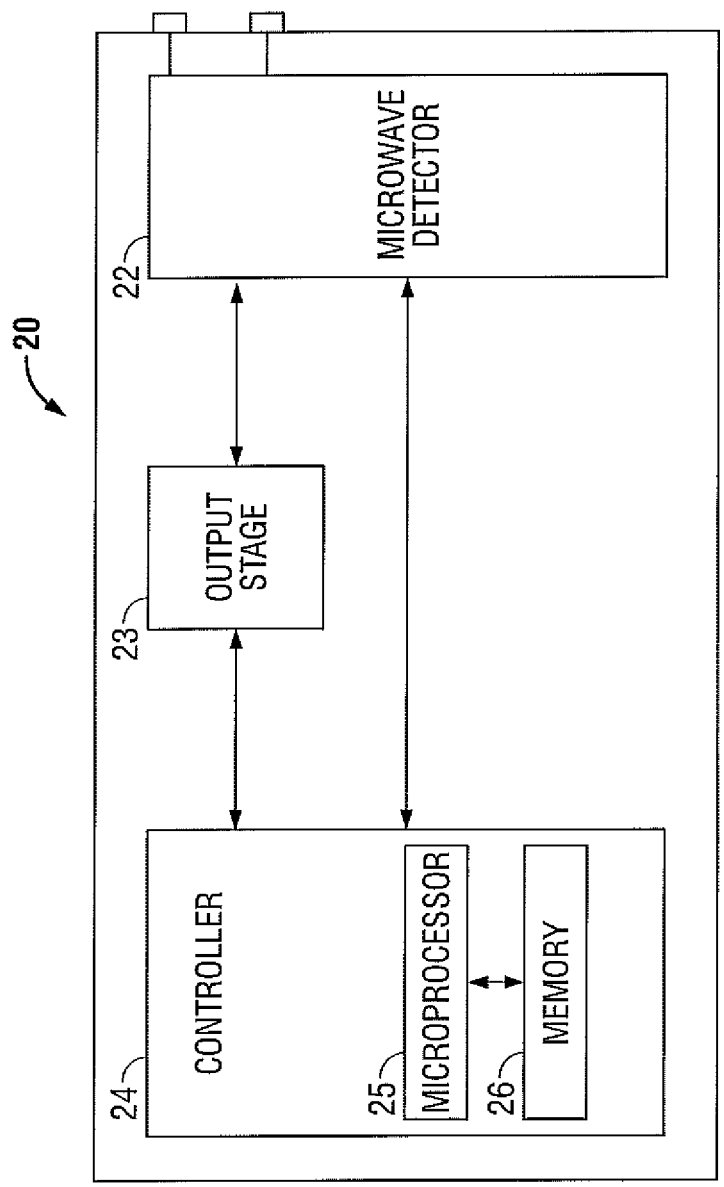
FIG. 2 is a schematic block diagram of a generator according to an embodiment of the present disclosure.

FIG. 2 shows a schematic block diagram of the generator 20. The generator 20 includes a controller 24, and an output stage 23. The controller 24 includes a microprocessor 25 operably connected to a memory 26, which may be volatile type memory (e.g., RAM) and/or non-volatile type memory (e.g., flash media, disk media, etc.). The controller 24 includes an output port that is operably connected to the output stage 23 allowing the microprocessor 25 to control the output of the generator 20 according to either open and/or closed control loop schemes. Those skilled in the art will appreciate that the microprocessor 25 may be substituted by any logic processor (e.g., control circuit) adapted to perform the control function discussed herein.

In a closed loop control scheme, a plurality of sensors measure a variety of tissue and energy properties (e.g., tissue impedance, tissue temperature, output current and/or voltage, reflected energy, absorbed energy, etc.), and provide feedback to the controller 24. The controller 24 then signals the output stage 23, which then adjusts the output power. The controller 24 also receives input signals from the input controls of the generator 20. The controller 24 utilizes the input signals to adjust power output by the generator 20 and/or performs other control functions thereon.

The therapeutic energy delivered to and applied to the tissue by the forceps 10 may be either RF or microwave energy or other forms that result in heating of the tissue. The forceps 10 is coupled to the generator 20 via a cable 11 adapted to transmit energy and control signals therebetween.

The forceps 10 is configured to support an end effector assembly 100. Forceps 10 typically includes various conventional features (e.g., a housing 60, a handle assembly 75, a rotating assembly 80, a trigger assembly 70) that enable forceps 10 and end effector assembly 100 to mutually cooperate to grasp, seal and, if warranted, divide tissue. Forceps 10 generally includes housing 60 and handle assembly 75, which includes moveable handle 62 and handle 72 that is integral with housing 60. Handle 62 is moveable relative to handle 72 to actuate end effector assembly 100 to grasp and treat tissue. Forceps 10 also includes a shaft 12 having a distal end 14 and a proximal end 16. The shaft 12 mechanically engages the end effector assembly 100 at its distal end 14 and the rotating assembly 80 and the housing 60 at its proximal end 16. Movement of rotating assembly 80 imparts similar rotational movement to shaft 12 which, in turn, rotates end effector assembly 100.

Figure 3:
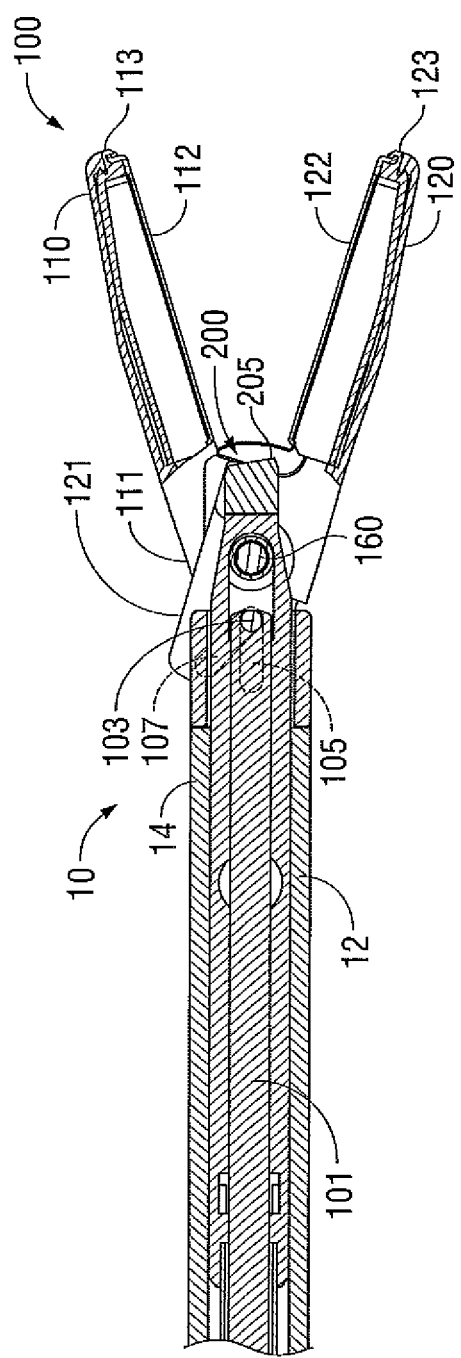
FIG. 3 is a cross-sectional view of a distal end of the forceps of FIG. 1.

Referring to FIG. 3, the end effector assembly 100 includes two jaw members 110 and 120 having proximal ends 111, 121 and distal ends 113, 123. Jaw members 110 and 120 are pivotable about a post 160 and are movable from a first position wherein jaw members 110 and 120 are spaced relative to another, to a second position wherein jaw members 110 and 120 are closed and cooperate to grasp tissue therebetween. As discussed in more detail below, the end effector assembly 100 may be adapted for use with various energy sources.

The shaft 12 houses a pushrod 101 that is operatively coupled to the movable handle 62 such that when the handle 62 is moved relative to the handle 72 the pushrod 101 moves longitudinally, either proximally or distally within the shaft 12. The pushrod 101 includes a push pin 103 disposed at the distal end 16 of shaft 12. Each of the jaw members 110 and 120 includes a slot 105 and 107, respectively, disposed at the proximal ends thereof. The slots 105 and 107 are in mechanical cooperation with the push pin 103, which is adapted to move within the slots 105 and 107. The pin 103 and slots 105 and 107 operate as a cam-follower mechanical linkage. Motion of the pushrod 101 causes the pin 103 to slide within respective slots 105 and 107. The slots 105 and 107 may be angled with respect to the distal ends of the jaws members 110 and 120 such that the members 110 and 120 move either toward or away from each other as the pushrod 101 is moved longitudinally in a proximal or distal direction, respectively.

The forceps 10 also includes a trigger assembly 70 that advances a knife 200 disposed within the end effector assembly 100. Once a tissue seal is formed, the user activates the trigger assembly 70 to separate the tissue along the tissue seal. Knife 200 includes a sharpened edge 205 for severing the tissue held between the jaw members 110 and 120 at the tissue sealing site.

Each jaw member 110 and 120 includes a sealing member 112 and 122, respectively, disposed on an inner-facing surface and/or within the jaw members 110 and 120. Sealing members 112 and 122 cooperate to seal tissue held between the jaw members 110 and 120 upon the application of energy. At least one of the sealing members 112 and 122 is connected to generator 20 that delivers energy to the tissue held therebetween.

In RF energy application, one or more of the sealing members 112 and 122 may be configured as electrosurgical electrodes that may be formed from one or more electrically conductive plates suitable for conducting RF energy to the tissue. The sealing members 112 and 122 are disposed on the inner-facing surfaces of the jaw members 110 and 120. More specifically, the cable 11 may couple the sealing members 112 and 122 to the generator and may be internally divided into one or more cable leads (not explicitly shown) that are designed to transmit electrical currents through their respective feed paths through the forceps 10 to the end effector assembly 100 such that energy is transmitted from the various cable leads to the respective feed paths and energy is transmitted to the tissue.

In microwave application, the sealing members 112 and 122 are configured as one or more microwave probes. In microwave energy application, the sealing members 112 and 122 may be disposed on the inner-facing surfaces or within the jaw members 110 and 120. The microwave probes are coupled to the generator 20, which is adapted to supply microwave energy to the forceps 10 through the cable 11, which may be configured as a coaxial cable suitable for delivery of microwave energy. The coaxial cable connects one or more of the microwave probes to the generator 20.

During operation tissue is grasped between the sealing members 110 and 120 and the generator 20 applies either RF or microwave energy thereto to seal the tissue. The output stage 23 also generates microwave monitoring signals that are transmitted to the target tissue. The output stage 23 may be an adjustable microwave signal generator capable of providing microwave signals in the range of 300 MHz to about 10,000 MHz, at signal power levels of up to 200 W. The output stage 23 is adjusted to provide the microwave monitoring and/or heating of the target tissue.

In one embodiment, the output stage 23 generates the microwave monitoring signals intermittently, interleaving the non-therapeutic microwave signals with therapeutic energy. If therapeutic RF energy is used in conjunction with microwave non-therapeutic signals, the output stage 23 may include two or more output stages to provide one output stage for therapeutic energy and another for the monitoring signals. In another embodiment, the output stage 23 may supply microwave monitoring signals continuously and simultaneously with the microwave therapeutic signals. In a further embodiment, if microwave energy is supplied therapeutically, the therapeutic signal may also be used as monitoring a signal.

Microwave energy delivered to the tissue is typically either absorbed by the tissue or reflected back to the generator 20. The microwave detector 22 is configured to determine absorbed microwave energy based on the measured reflected and/or absorbed microwave energy. Absorbed microwave energy may be determined by subtracting measured reflected energy from the total incident energy supplied by the generator 20. The amount of microwave energy absorbed by the tissue depends on the hydration of the tissue and the amount and geometry of the tissue within the jaws.

The output and reflected microwave signals are measured with the microwave detector 22. The measured amplitude of the output and reflected microwave signals are then transmitted to the controller 24 which analyzes the amplitudes over time to determine the current state of the target tissue including, but not limited to, desiccation, hydration, impedance, and combinations thereof, and/or the appropriate response of the tissue sealing system. The controller 24 is also programmed or otherwise configured to adjust the therapeutic energy of the generator 20 based on the measured state of the target tissue.

The microwave detector 22 may be tunable to a selected band of frequencies in the microwave range, more particularly, in the frequency range of the reflected and/or absorbed microwave monitoring signals. The measured monitoring signals are then transmitted to the controller 24, which then analyzes the signals to determine the completeness of the seal. The controller 24 is also programmed or otherwise configured to adjust the therapeutic energy of the generator 20 based on the detected seal parameters.

Figure 4:
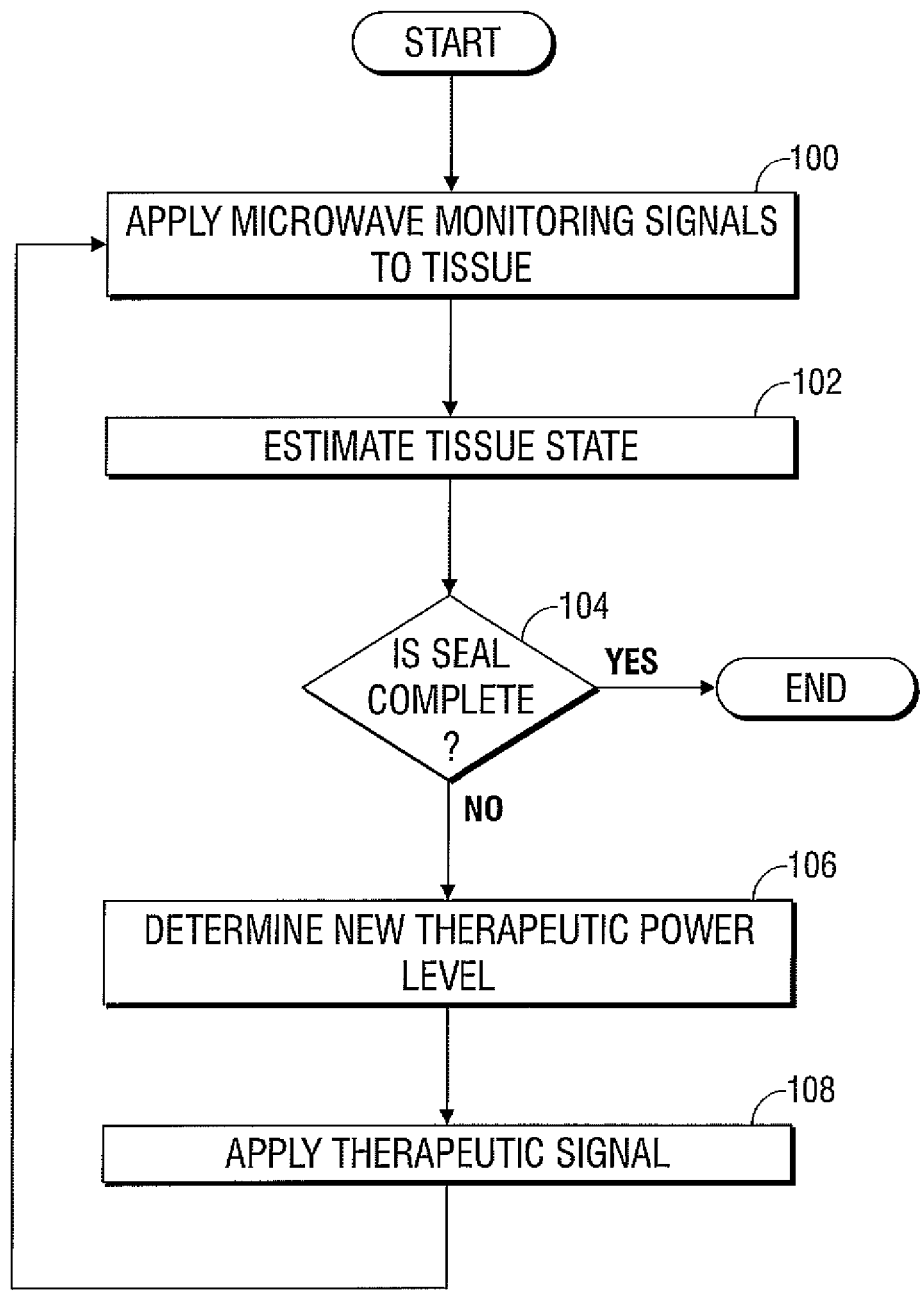
FIG. 4 is a flow chart illustrating a method according to another embodiment of the present disclosure.

FIG. 4 illustrates a method for controlling a sealing procedure based on the state of the tissue as measured by the microwave monitoring signals. The method may be implemented as an algorithm that controls the power applied to the tissue by the generator 20 and the forceps 10, so that a completed seal is achieved. The algorithm may be embodied as any type of suitable machine-readable code stored in the memory 26 and executable by the controller 24 and/or the microprocessor 25.

Many different possible control algorithms may exist, and therefore the example described below is intended to be illustrative rather than exclusive. In step 100, the output stage 23 transmits an initial non-therapeutic microwave monitoring signals. The monitoring signals may be supplied at varying intensities and microwave frequencies. The response of the tissue-jaw system is measured and recorded.

In step 102, the state of the tissue is estimated based on the measured response of the tissue-jaw system. If the seal is complete, step 104 directs the algorithm to terminate. If the seal is not complete, step 106 is executed. In step 106, a new therapeutic power level is determined. Then, in step 108, the new therapeutic signal is applied. At this point, a new control cycle begins with the application of the microwave monitoring signals, step 100. Many variations of this algorithm may be realized including variants such as, where the therapeutic and monitoring signals are applied simultaneously and/or continuously, where the therapeutic signal is used as the monitoring signal, and the like.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for monitoring tissue state during a tissue sealing procedure, the system comprising:
    a forceps including opposing jaw members movable from a first position in spaced relation relative to one another to at least one subsequent position wherein the jaw members cooperate to grasp tissue therebetween; and
    a generator coupled to at least one of the jaw members, the generator including:
    an output stage configured to generate therapeutic energy and non-therapeutic microwave monitoring signals;
    a microwave detector configured to measure at least one of absorbed or reflected non-therapeutic microwave monitoring signals, the microwave detector being tunable to a selected frequency band in a frequency range of the non-therapeutic microwave monitoring signals; and a controller operatively coupled to the microwave detector, the controller configured to determine state of the tissue based on at least one of the absorbed or reflected non-therapeutic microwave monitoring signals and to control the delivery of therapeutic energy from the generator to tissue based the state of the tissue.

2. The system according to claim 1, wherein the microwave detector is configured to determine absorption of non-therapeutic microwave monitoring signals.

3. The system according to claim 1, wherein the output stage is configured to interleave the non-therapeutic microwave monitoring signals with the therapeutic energy.

4. The system according to claim 1, wherein the output stage is configured to generate the non-therapeutic microwave monitoring signals simultaneously with the therapeutic energy.

5. The system according to claim 1, wherein the output stage is configured to generate therapeutic energy selected from the group consisting of a high frequency RF energy from about 100 kHz to about 300 MHz and microwave energy from about 300 MHz to about 10,000 MHz.

6. A system for monitoring tissue state during a tissue sealing procedure, the system comprising:
   a forceps including opposing jaw members configured to grasp tissue therebetween, at least one of the jaw members including at least one microwave probe; and
   a generator coupled to the at least one microwave probe, the generator including:
   a microwave output stage configured to generate therapeutic microwave energy;
   a microwave detector configured to measure at least one of absorbed or reflected therapeutic microwave energy, the microwave detector being tunable to a selected frequency band in a frequency range of the non-therapeutic microwave monitoring signals; and
   a controller operatively coupled to the microwave detector, the controller configured to determine state of the tissue based on at least one of the absorbed or the reflected therapeutic microwave energy and to control the delivery of the therapeutic energy from the generator to tissue based the determined state of the tissue.

7. The system according to claim 6, wherein the microwave detector is tuned to a selected band of frequencies in a frequency range of the absorbed therapeutic microwave energy.

8. The system according to claim 6, wherein the output stage is configured to generate therapeutic microwave energy having a frequency from about 300 MHz to about 10,000 MHz.

9. A method for monitoring tissue state during a tissue sealing procedure, the method comprising:
   supplying therapeutic energy and non-therapeutic microwave monitoring signals to a forceps, the forceps including opposing jaw members configured to grasp tissue therebetween; measuring reflected non-therapeutic microwave monitoring signals;
   tuning a microwave detector to a selected frequency band in a frequency range of the non-therapeutic microwave monitoring signals; and
   controlling the delivery of therapeutic energy based on reflected non-therapeutic microwave monitoring signals.

10. The method according to claim 9, wherein the microwave detector is configured to determine absorption of non-therapeutic microwave monitoring signals.

11. The method according to claim 9, wherein supplying step further includes the step of interleaving the non-therapeutic microwave monitoring signals with the therapeutic energy.

12. The method according to claim 9, wherein supplying step further includes the step of generating the non-therapeutic microwave monitoring signals simultaneously with the therapeutic energy.

13. The method according to claim 9, wherein supplying step further includes the step of generating therapeutic energy selected from the group consisting of a high frequency RF energy from about 100 kHz to about 300 MHz and microwave energy from about 300 MHz to about 10,000 MHz.

* * * * *